United States Patent [19]

Anderson

[11] Patent Number: 4,594,064
[45] Date of Patent: Jun. 10, 1986

[54] AUTOMATED APPARATUS FOR PRODUCING GRADIENT GELS

[75] Inventor: Norman L. Anderson, Clarendon Hills, Ill.

[73] Assignee: The United States of America as represented by the United States Department of Energy

[21] Appl. No.: 550,429

[22] Filed: Nov. 10, 1983

[51] Int. Cl.[4] .................. B29C 31/10; G01N 27/28
[52] U.S. Cl. ........................... 425/145; 425/147; 425/257; 425/258; 204/299 R
[58] Field of Search ............... 204/299 R, 180 G; 425/130, 135, 140, 147, 150, 256, 258, 257

[56] References Cited

U.S. PATENT DOCUMENTS

| | | | |
|---|---|---|---|
| 3,706,515 | 12/1972 | Keuerleber et al. | 425/257 |
| 4,035,377 | 7/1977 | Detroy | 204/299 R |
| 4,088,561 | 5/1978 | Anderson | 204/299 R |
| 4,102,367 | 7/1978 | Shulman et al. | 425/258 |
| 4,119,304 | 10/1978 | Groom | 425/130 |
| 4,169,036 | 9/1979 | Anderson et al. | 204/299 R |

Primary Examiner—John F. Niebling
Assistant Examiner—B. J. Boggs, Jr.
Attorney, Agent, or Firm—William Lohff; James W. Weinberger; Judson R. Hightower

[57] ABSTRACT

Apparatus for producing a gradient gel which serves as a standard medium for a two-dimensional analysis of proteins, the gel having a density gradient along its height formed by a variation in gel composition, with the apparatus including first and second pumping means each including a plurality of pumps on a common shaft and driven by a stepping motor capable of providing small incremental changes in pump outputs for the gel ingredients, the motors being controlled, by digital signals from a digital computer, a hollow form or cassette for receiving the gel composition, means for transferring the gel composition including a filler tube extending near the bottom of the cassette, adjustable horizontal and vertical arms for automatically removing and relocating the filler tube in the next cassette, and a digital computer programmed to automatically control the stepping motors, arm movements, and associated sensing operations involving the filling operation.

5 Claims, 1 Drawing Figure

AUTOMATED APPARATUS FOR PRODUCING GRADIENT GELS

CONTRACTUAL ORIGIN OF THE INVENTION

The U.S. Government has rights in this invention pursuant to Contract No. W-31-109-ENG-38 between the U.S. Department of Energy and The University of Chicago representing Argonne National Laboratory.

BACKGROUND OF THE INVENTION

This invention relates to an automatic system for sequentially filling a plurality of slab-gel holders with a coagulable or polymerizable gel solution having a continuous variation in density to provide a gel having a density gradient along its height. The gel is useful as a standard medium in the analysis of proteins by two-dimensional electrophoresis to form two-dimensional protein maps. More particularly, the invention relates to an automatic system for filling the slab-gel holders to control gel variation between gels in a plurality of slab-gel holders and for automatically indexing or advancing from one slab-gel holder to another holder as each holder is filled.

The gels are used for electrophoresis separation of proteins for protein analysis and identification. The procedure begins with the isoelectric separation of protein species along a thin, elongated or spaghetti-like gel medium. In this original separation, the proteins migrate to a previously established pH point within the gel at which the sample is electrically neutral. These separations are quite well known and can be followed by a second dimensional electrophoresis separation to provide a high resolution of protein and protein subunits. In the electrophoresis separation, sample protein species migrate through a gel acting as a sieve to a point determined by their molecular weight.

The initial isoelectric separation and the second electrophoresis separation are both described in the assignee's U.S. Pat. No. 4,088,561 issued May 9, 1978, entitled "Apparatus for Electrophoresis Separation." This patent is expressly incorporated herein by reference. The electrophoresis separation is performed across an acrylamide gel containing sodium dodecyl sulfate (SDS) employed to negate the proteins' intrinsic charges. Gel compositions are well known and include polymerizable monomers as well as cross linking agents, catalysts and iniators, along with a gel buffer. Apparatus associated with the filling operation are described in assignee's U.S. Pat. No. 4,169,036.

In the past, the slab-gel holders have been filled manually in a batch-wise manner. This has required considerable effort in controlling gel variation between batches of gels to provide a plurality of standard gels. The production of standard gels is important not only for the accuracy of the protein analysis at a particular laboratory but also to control variation in standard gels at different facilities to provide results which may be transferred between those facilities.

Accordingly, one object of this invention is to provide apparatus for sequentially filling a plurality of slab-gel holders not limited to a fixed batch size. Another object of the invention is to provide apparatus for automatically controlling the filling operation and for transferring the filling apparatus from holder to holder. Another object is to provide a mechanism for quickly computing and producing one or a series of new gradient formulations for test and optimization. These and other objects will become apparent from the following detailed description.

SUMMARY OF THE INVENTION

Briefly, this invention is directed to apparatus for automatically producing a gradient gel which serves as a standard medium for a two-dimensional analysis of proteins, the gel having a density gradient along its height formed by a variation in gel composition. The apparatus comprises (1) mixing means for forming said gel composition from different (usually light and heavy) combinations of gel ingredients, (2) first and second means for transferring the combinations to the mixing means including first and second pumping means, (3) motor means for incrementally driving the pumping means, (4) a hollow form or cassette for receiving the gel composition, (5) means for transferring the gel composition from the mixing means to the form with a filler tube extending into the form (generally near the bottom), (6) arm means for sequentially withdrawing and relocating the filler tube in the next adjacent cassette and (7) digital computer means for providing digital signals to the motor means and arm means. In one embodiment as illustrated in FIG. 1, the computer provides digital signals to sequentially drive stepping motors and vertical and horizontal adjustment arms. The computer is programmed to control the rate of pumping of each of the gel formulations identified as light and heavy combinations of gel ingredients. The stepper motors permit pumping a small increment of each gel ingredient simultaneously for each set of gel ingredients. In addition, the arms are adjusted by a series of incremental movements for the filling tube to be removed and relocated for the next filling operation.

DETAILED DESCRIPTION OF THE PREFERRED EMBODIMENT

Figure 1:
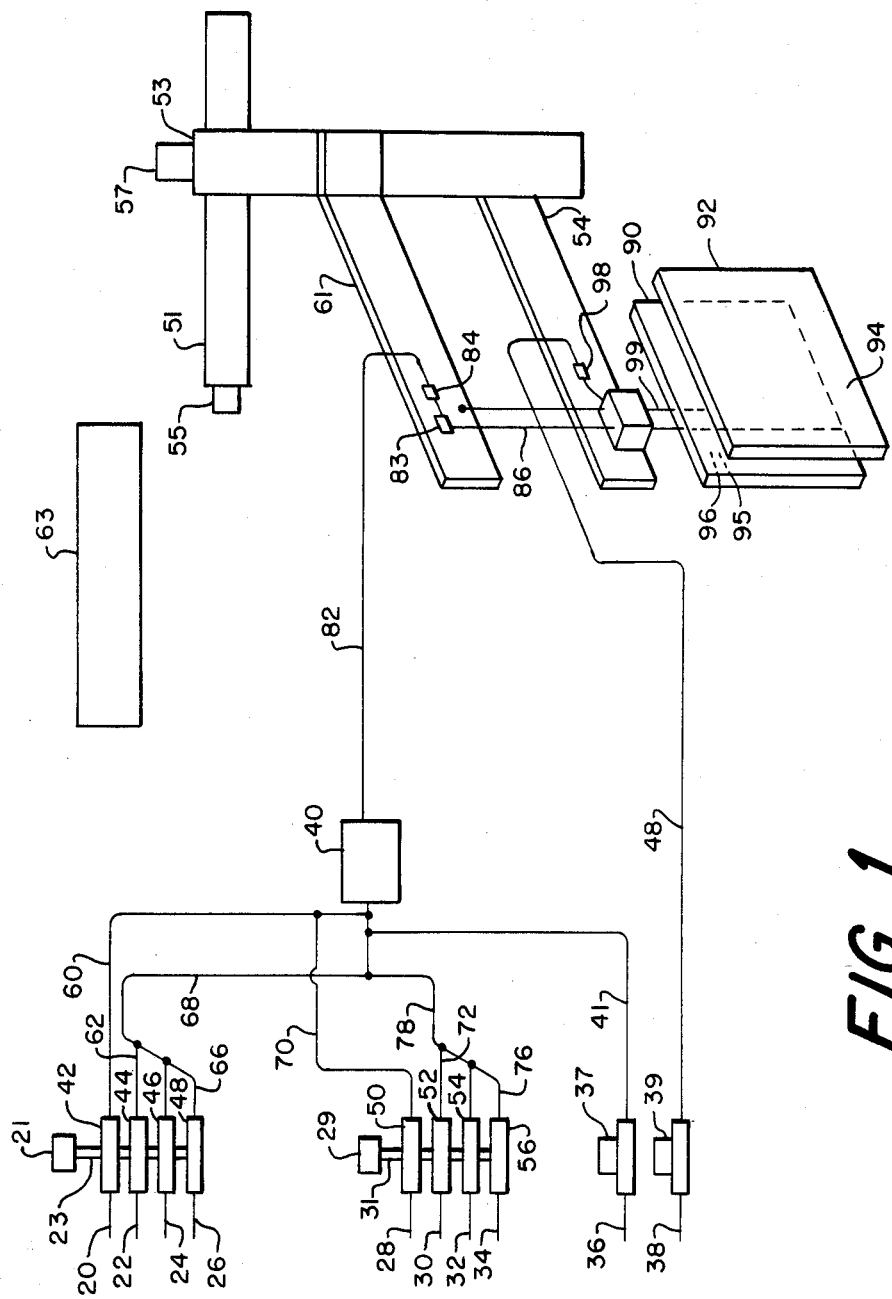
FIG. 1 is a schematic of an apparatus representing one embodiment of this invention.

The apparatus embodying this invention includes a plurality of means for transferring a plurality of gel ingredients to mixing means. For mixing two combinations of gel ingredients as illustrated in FIG. 1, the transfer means includes two sets of pumps arranged on a common shaft and associated connecting lines. These pumps are driven by motor means which preferably are stepper motors to drive the pumps by a series of small incremental movements to provide accurate control of gel ingredients to the mixer.

A gel composition is provided in the mixer and is transferred via the associated lines to a hollow form or cassette in which a filler tube provides access to a position near the bottom of the cassette.

In the filling operation, means are provided for limiting the gel composition to a predetermined height in the cassette. In the illustrated embodiment, a predetermined amount of gel composition is provided to the cassette and any deviation in height is corrected by the addition of a small quantity of the heavy gel combination at the bottom of the cassette. The limiting means includes a sensor which is actuated electrically as the level reaches a predetermined height to shut off a valve. After the desired height of gel composition is achieved, an upper protective layer is provided over the gel composition by means of a shorter filling tube which also connects the sensor to the liquid.

Arm means are provided for automatically withdrawing and relocating the filling tubes and includes adjustable vertical and horizontal arms. Means are provided for adjusting this arm to sequentially withdraw the tubes and relocate them in the next adjacent cassette.

A digital computer provides a series of signals to the stepper motors to sequentially actuate the motors. Preferably, compositional gradients are made by a method such that a pulse actuates the first motor and the absence of a pulse actuates the second motor according to a program loaded in the computer. The computer further provides after the filling operation is completed, a series of digital signals to operate the arm means to move the filler tubes to the next cassette.

In the embodiment illustrated in FIG. 1, individual streams of gel ingredients are provided by lines 20-26 for the lower density or light gel formula, lines 28-34 for the higher density or heavy gel formula, and lines 36-38 for water and a gel cover formulation (a detergent formulation) identified as "Photoflo" made by Eastman Kodak, respectively. Typical formulae for a gel formula includes a gel-forming monomer such as acrylamide available from lines 20 and 28, a buffer providing pH control and available from lines 22 and 30, a gel catalyst available from lines 24 and 32 and a polymerization initiator available from lines 26 and 34. As illustrated, the individual gel ingredients for each formula are fed to the mixer 40 by individual pumps 42-48 for the lower density gel and 50-56 for the higher density gel. Each set of ingredients for a particular gel is pumped at a predetermined relative rate to provide a predetermined formula. As illustrated, the acrylamide from lines 60 and 70 are combined apart from the other ingredients and fed to mixer 40. The remaining three ingredients for each formula are fed via lines 62-66 to line 68 and via lines 72-76 to line 78. Water is also provided by pump 37 and line 41 to mixer 40.

In mixer 40, the ingredients are mixed to form a gel composition which is transferred via line 82 to feed line 86 and into hollow form 90. Valve 84 is provided as a means of disconnecting the flow when a predetermined amount of gel is provided. As illustrated, feed line 86 extends close to the bottom 94 of cassette 90. During the filing operation, the cassette 92 is filed to a height 95 which may vary slightly because of the slight variance of the inner dimensions of cassette 92. Therefore, an additional amount of the higher density gel is fed to the cassette to provide a predetermined height 96 when a level sensor 98 shuts off the flow. Sensor 98 includes line 99 which provides a feed line for the Photoflo (fed via pump 39 and line 48 to line 99) and is connected electrically to tube 86.

Means for retracting the feed lines 86 and 99 are provided by movable arms 61 and 53 which may be adjusted horizontally and vertically by lead screw sliders 55 and 57, and by arms 54 and 61 which carry the feed lines. Arm 54 is mounted in a fixed position while arm 61 is moved vertically by lead screw slider 57.

When the filing operation of cassette 90 is completed, lead screw 57 acts to move arm 61 to retract feed lines 86 and 99. Lead screw slider 55 then acts to move arm 53, 54 and 61 to a new position over cassette 92. The horizontal and vertical adjustments are made by digital signals and therefore, the movement is by incremental steps. The final adjustment is accomplished by feed line 86 acting as a probing sensor to sense an opening in cassette 92. If movement line 86 is restricted, switch 83 is activated to stop the downward movement and the horizontal position is adjusted. When an opening is located, the feed line 86 is lowered to the final position.

Computer 63 provides the preprogrammed signals for stepper motors 21 and 29 and for the movement of arms 51 and 53. As illustrated, stepper motors 21 and 29 are each connected to the individual pumps by shafts 23 and 31.

Additional objects, advantages and novel features of the invention will be set forth in part in the description which follows, and in part will become apparent to those skilled in the art upon examination of the following or may be learned by practice of the invention.

The embodiments of the invention in which an exclusive property or privilege is claimed are defined as follows:

1. Apparatus for producing a gradient gel having a variation in composition along the height of the gel, the gel being useful as in providing a standard medium for a two-dimensional electrophoretic analysis of proteins and having a density gradient along said height resulting from said variation in composition, the apparatus comprising:
   mixing means for forming said gel composition from light and heavy combinations of gel ingredients,
   first and second means for transferring the light and heavy combinations of gel ingredients to said mixing means including first and second pumping means,
   motor means for incrementally driving said pumping means for providing a predetermined quantity of said light and heavy combinations of gel ingredients,
   a hollow form for receiving said gel composition,
   first transfer means including a first filler tube for transferring said gel composition from said mixing means to said hollow form to provide a predetermined amount of said gel composition in said form, the filler tube extending to a position near the bottom of the form,
   adjustment means for adding a small quantity of said heavy combination of gel ingredients through said first filler tube to move said gel composition to a predetermined height,
   means for limiting the gel composition to said predetermined height in said form,
   arm means for sequentially withdrawing the filler tube and relocating said tube in an opening in the next adjacent hollow form, including vertical and horizontal adjustment means, and
   digital computer means for providing digital signals to drive said motor means and said arm means.

2. The apparatus of claim 1 wherein each of said first and second pumping means includes a plurality of pumps connected to a common shaft and wherein said motor means includes first and second stepper motors, each connected to one of said shafts.

3. The apparatus of claim 2 including means for providing an upper protective layer over said gel composition.

4. The apparatus of claim 3 wherein said arm means includes vertical and horizontal moveable arms for withdrawing and relocating said filler tube.

5. The apparatus of claim 4 wherein said computer means provides sequential operation of said motors and said arm means.

* * * * *